United States Patent
Chiesl

(10) Patent No.: US 9,441,265 B2
(45) Date of Patent: Sep. 13, 2016

(54) COMPOSITIONS AND METHODS FOR SAMPLE PREPARATION

(71) Applicant: IBIS BIOSCIENCES, INC., Carlsbad, CA (US)

(72) Inventor: Thomas N. Chiesl, Hurcules, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 14/369,627

(22) PCT Filed: Dec. 28, 2012

(86) PCT No.: PCT/US2012/072073
§ 371 (c)(1),
(2) Date: Jun. 27, 2014

(87) PCT Pub. No.: WO2013/102080
PCT Pub. Date: Jul. 4, 2013

(65) Prior Publication Data
US 2014/0363822 A1    Dec. 11, 2014

Related U.S. Application Data

(60) Provisional application No. 61/581,504, filed on Dec. 29, 2011.

(51) Int. Cl.
| | | |
|---|---|---|
| *C12Q 1/68* | (2006.01) | |
| *C12N 1/06* | (2006.01) | |
| *C12M 1/00* | (2006.01) | |
| *C12M 1/33* | (2006.01) | |
| *C12M 3/08* | (2006.01) | |
| *G01N 33/552* | (2006.01) | |
| *C12N 15/10* | (2006.01) | |

(52) U.S. Cl.
CPC ......... *C12Q 1/6806* (2013.01); *C12N 15/1006* (2013.01)

(58) Field of Classification Search
CPC ...... C12Q 1/68; C12M 1/34; C12N 15/1006; G01N 33/52
USPC ............. 435/6.1, 259, 283.1, 306.1; 436/527
See application file for complete search history.

(56) References Cited

U.S. PATENT DOCUMENTS

| | | | |
|---|---|---|---|
| 5,447,864 A | 9/1995 | Raybuck et al. | |
| 5,650,506 A | 7/1997 | Woodard et al. | |
| 5,688,642 A * | 11/1997 | Chrisey et al. | 435/6.11 |
| 5,705,628 A | 1/1998 | Hawkins | |
| 5,898,071 A | 4/1999 | Hawkins | |
| 6,165,905 A | 12/2000 | Annapragada | |
| 6,746,608 B2 | 6/2004 | Smiley | |
| 2006/0243658 A1* | 11/2006 | Zubov et al. | 210/502.1 |
| 2008/0213853 A1* | 9/2008 | Garcia et al. | 435/173.1 |
| 2010/0331522 A1 | 12/2010 | Irvine et al. | |
| 2011/0240130 A1 | 10/2011 | Den Dulk et al. | |
| 2011/0256566 A1* | 10/2011 | Schweigert | G01N 1/4055 435/19 |

FOREIGN PATENT DOCUMENTS

WO    9721090 A1    6/1997

OTHER PUBLICATIONS

Cheng J., et al., "Chip Pcr. II. Investigation of Different Pcr Amplification Systems in Microbabricated Silicon-glass Chips," Nucleic Acids Research, 1996, vol. 24 (2), pp. 380-385.
Chomczynski P., et al., "Dnazol: A Reagent for the Rapid Isolation of Genomic Dna," Biotechniques, 1997, vol. 22 (3), pp. 550-553.
Christel L.A., et al., "Rapid, Automated Nucleic Acid Probe Assays Using Silicon Microstructures for Nucleic Acid Concentration," Journal of Biomechanical Engineering, 1999, vol. 121 (1), pp. 22-27.
Hofmann M.A., et al., "Sequencing Pcr Dna Amplified Directly from a Bacterial Colony," Biotechniques, 1991, vol. 11 (1), pp. 30-31.
International Search Report and Written Opinion for Application No. PCT/US2012/072073, mailed on Mar. 13, 2013, 15 pages.
Leadon S.A., et al., "A Rapid and Mild Procedure for the Isolation of Dna from Mammalian Cells," Analytical Biochemistry, 1982, vol. 120 (2), pp. 282-288.
Longmire J.L., et al., "A Rapid and Simple Method for the Isolation of High Molecular Weight Cellular and Chromosome-specific Dna in Solution Without the Use of Organic Solvents," Nucleic Acids Research, 1987, vol. 15 (2), pp. 859.
Service R.F., "Coming Soon: the Pocket Dna Sequencer," Science, 1998, vol. 282 (5388), pp. 399-401.

* cited by examiner

*Primary Examiner* — Narayan Bhat
(74) *Attorney, Agent, or Firm* — David A. Casimir; Casimir Jones, S.C.

(57) ABSTRACT

The invention relates generally to compositions and methods for disrupting cells (e.g., disrupting cellular and nuclear membranes). In particular, the invention provides modified solid surfaces (e.g., bead surfaces) and their use in disruption of cellular membranes (e.g., during cellular lysis procedures (e.g., for recovery of nucleic acid (e.g., DNA or RNA) from mechanical cell lysis)). Compositions and methods of the invention find use in a wide range of applications including molecular biology and medical science.

13 Claims, 1 Drawing Sheet

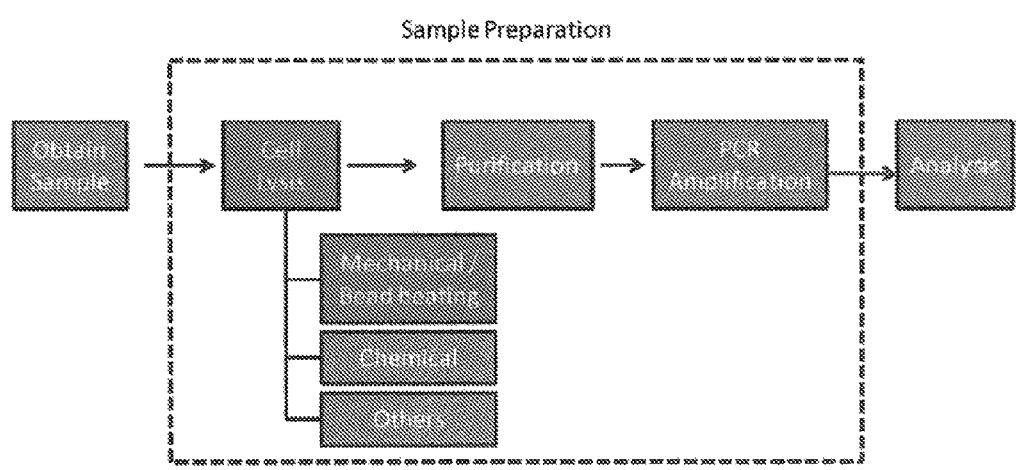

COMPOSITIONS AND METHODS FOR SAMPLE PREPARATION

CROSS-REFERENCE TO RELATED APPLICATIONS

The present Application claims priority to U.S. Provisional Application Ser. No. 61/581,504 filed Dec. 29, 2011, the entirety of which is incorporated by reference herein.

FIELD OF THE INVENTION

The invention relates generally to compositions and methods for disrupting cells (e.g., disrupting cellular and nuclear membranes). In particular, the invention provides modified solid surfaces (e.g., bead surfaces) and their use in disruption of cellular membranes (e.g., during cellular lysis procedures (e.g., for recovery of nucleic acid (e.g., DNA or RNA) from mechanical cell lysis)). Compositions and methods of the invention find use in a wide range of applications including molecular biology and medical science.

BACKGROUND OF THE INVENTION

There is a requirement to isolate DNA rapidly and conveniently from a variety of cellular sources, including blood. The availability of DNA has greatly facilitated the analysis and characterization of the genome in many organisms through the application of sequencing and hybridization techniques. Conventional approaches to DNA isolation and purification are based on multi-step procedures involving phenol/chloroform (See, e.g., Sambrook, J. et al, Molecular Cloning: A Laboratory Manual, $2^{nd}$ Edition, Cold Spring Harbor Laboratory Press, 1989). These processes are inherently laborious, may result in damaged DNA samples and are generally not amenable to automation. A number of non-toxic extraction procedures have been reported (See, e.g., Nucleic Acids Research, 15, 859, 1987; Analytical Biochemistry, 120, 282 288 1982), but require either extensive dialysis or use of filters. Other extraction methods include the use of chaotropic agents (See, e.g., BioTechniques, 22, 550 553, 1997) or are applicable only to specific cell types and involve lysis, dilution and addition to a PCR tube (See, e.g., BioTechniques, 11, 30 31, 1991).

SUMMARY OF THE INVENTION

The invention relates generally to compositions and methods for disrupting cells (e.g., disrupting cellular and nuclear membranes). In particular, the invention provides modified solid surfaces (e.g., bead surfaces) and their use in disruption of cellular membranes (e.g., during cellular lysis procedures (e.g., for recovery of nucleic acid (e.g., DNA or RNA) from mechanical cell lysis)). Compositions and methods of the invention find use in a wide range of applications including molecular biology and medical science.

Accordingly, in an embodiment, the invention provides a method of isolating nucleic acid from a sample comprising contacting the sample with a composition comprising a fluorinated organic group modified surface; mechanically disrupting the sample; and isolating nucleic acid from the disrupted sample. The invention is not limited by the type of composition (e.g., material) that is modified with a fluorinated organic group. Indeed, any number of compositions/materials utilized in disrupting a sample (e.g., lysing or otherwise disrupting a sample (e.g., cell sample)) may be modified including, but not limited to, beads, containers and the like. In some embodiments, the composition comprising a modified surface is a silica bead. In some embodiments, the bead is between 90 µm and 500 µm in size, although smaller and large beads may be used. The invention is not limited by the type of fluorinated organic group used for modification. In a preferred embodiment, the fluorinated organic group is a fluorinated silane. In a further preferred embodiment, the fluorinated silane is perfluorooctyltriethoxysilane. In some embodiments, the composition comprising a fluorinated silane modified surface has less affinity for nucleic acid than an identical composition without a fluorinated silane modified surface. In some embodiments, the nucleic acid is DNA. In other embodiments, the nucleic acid is RNA. In some embodiments, the sample is a mammalian or microbial cell.

The invention also provides compositions and/or materials used to disrupt or lyse cells comprising a fluorinated organic group modified surface. In a preferred embodiment, the fluorinated organic group is a fluorinated silane. In a further preferred embodiment, the fluorinated silane is perfluorooctyltriethoxysilane. The invention is not limited by the composition/material) used to disrupt or lyse cells. Indeed, any number of compositions/materials utilized to disrupt or lyse cells may be used including, but not limited to, beads, containers and the like. In some embodiments, the material is a silica bead. In some embodiments, the material is a container. In some embodiments, the number of reactive —OH groups on the material is reduced due to fluorinated organic group modification.

BRIEF DESCRIPTION OF THE DRAWINGS

FIG. 1 depicts a generalized sample preparation scheme.

DETAILED DESCRIPTION OF THE INVENTION

The invention relates generally to compositions and methods for disrupting cells (e.g., disrupting cellular and nuclear membranes). In particular, the invention provides modified solid surfaces (e.g., bead surfaces) and their use in disruption of cellular membranes (e.g., during cellular lysis procedures (e.g., for recovery of nucleic acid (e.g., DNA or RNA) from mechanical cell lysis)). Compositions and methods of the invention find use in a wide range of applications including molecular biology and medical science.

A number of methods have been used to isolate DNA from samples. For example, U.S. Pat. No. 5,650,506 relates to modified glass fiber membranes which exhibit sufficient hydrophilicity and electropositivity to bind DNA from a suspension containing DNA and permit elution of the DNA from the membrane. The modified glass fiber membranes are useful for purification of DNA from other cellular components. A product is also available based on isolation of DNA from blood on glass filters (See, e.g., GFX, Genomic Blood DNA Purification Kit, AMERSHAM PHARMACIA Biotech). U.S. Pat. Nos. 5,705,628 and 5,898,071 disclose a method for separating polynucleotides, such as DNA, RNA and PNA, from a solution containing polynucleotides by reversibly and non-specifically binding the polynucleotides to a solid surface, such as a magnetic microparticle. A similar approach has been used in a product, "DYNABEADS DNA Direct" marketed by DYNAL A/S, Norway. Similarly, glass, plastic and other types of beads have been used to bind to and isolate DNA from solutions.

U.S. Pat. No. 5,447,864 discloses a method of separating cell nuclei from cells by means of a pipette tip device, open at one end and having a membrane extending across its forward end. The method comprises treating a fluid containing whole cells so as to selectively lyse the cytoplasmic membrane, together with a small proportion of the nuclear membranes, but leaving a large proportion of the cell nuclei intact. The treated fluid is applied to the membrane whereby a mesh of DNA from the lysed nuclei is formed on the surface and captures intact cell nuclei. The mesh comprising DNA on the surface is then washed to separate the captured cell nuclei from other components of the cells. A device for use in the method is also described, the device comprising a pipette tip having a membrane that extends across its forward end.

Methods for the isolation of DNA in microstructured devices have demanded substantial simplification of conventional techniques that are time-consuming and frequently require centrifugation, pipetting, vortexing or thermal incubation steps. One approach to the purification of DNA from whole blood is to isolate the white blood cells prior to direct PCR (See, e.g., Nucleic Acids Research, 24, 380 385, 1996), thus removing a primary inhibitor of PCR, namely haemoglobin. Another approach (See, e.g., Science, 282, 399 401, 1998) involves mixing blood with a salt solution that lyses the cells. The lysate is then introduced into a chamber containing a glass wall on which DNA binds by charge interaction, while the rest of the sample is ejected. The DNA is washed with ethanol/water mixes and then eluted to a neighbouring chamber.

WO 97/21090 relates to methods and apparatus for performing micro-analytic and micro-synthetic procedures. The invention provides an apparatus comprising a rotatable disc which includes sample inlet port, fluid micro-channels, reaction chambers and outlet ports. Movement of fluids within the device, for example reagents, samples and other liquid components, is facilitated by rotation of the disc causing centripetal acceleration of the fluids through the micro-channels embedded in the disc. Methods specific for the apparatus are provided for performing a variety of procedures, including DNA synthesis, micro-extraction and cell counting.

A method for the extraction and concentration of short (500 bp) and medium size (48000 bp) DNA from test samples of bacteriophage lambda DNA utilizing silicon fluidic microchips is disclosed in J. Biomechanical Engineering, 121, 23 27 (1999).

The present invention relates generally to compositions and methods for disrupting cells (e.g., disrupting cellular and nuclear membranes). In particular, the invention provides modified solid surfaces (e.g., bead surfaces) and their use in disruption of cellular membranes (e.g., during cellular lysis procedures (e.g., for recovery of nucleic acid (e.g., DNA or RNA) from mechanically lysed cells)). Compositions and methods of the invention find use in a wide range of applications including molecular biology and medical science.

Accordingly, in some embodiments, the invention provides compositions comprising modified (e.g., chemically modified) surfaces (e.g., bead surfaces (e.g., glass, plastic, metal or other type of bead surface) or a container surface) that improve nucleic acid (e.g., DNA or RNA) recovery during cell lysis (e.g., lysis of cells via mechanical, chemical or other method) and methods of using the same. In a preferred embodiment, a composition comprising a modified surface (e.g., of a substance used for cell disruption and/or lysis (e.g., a bead surface or a container surface) is generated via modification of the surface with one or more organic reagents (e.g., fluorinated organic (e.g., organo-silico) reagents (e.g., fluorinated silanes (that reduce adsorption of nucleic acid molecules (e.g., DNA and RNA molecules) onto the bead and/or container surface))).

In some embodiments, a modifying reagent utilized herein is perfluorooctyltriethoxysilane; however, the invention is not limited to this fluorinated silane. For example, compositions and methods of the invention may utilize a reagent that comprises at least one reactive group to bond to a surface (e.g., a bead or container surface) and a fluorinated organic group to reduce the surface energy of the surface (e.g., a bead or container surface). Example reactive groups include, but are not limited to, chlorosilane, methoxysilane, ethoxysilane. The reactive group may contain one or more active components to react with the surface (e.g., di- or tri-chloro silane/di- or tri-ethoxy silane). The fluorinated organic group can contain at least one carbon and at least one fluorine. Aromatic and aliphatic carbons may be used. Polymeric silinating agents also find use within the scope of the invention. A polymer silinating agent comprises multiple reactive groups (e.g., multiple reactive silane groups) and/or where the fluorinated carbon is a fluorinated polymer comprising 1-20 or more carbons and/or fluorine molecules. Molecules that need to first be activated to become reactive with a surface (e.g., glass surface) also find use in the invention. For example, a reagent that needs to be treated with acid or base before it will react with a substrate —OH bond is also useful in the compositions and methods described herein.

As used herein, the term "bead" is not meant as being restricted to spherical objects but rather encompasses particulate matter without limitation to shape. Beads may be between about 90 μm and 500 μm in size (e.g., about 100, 125, 150, 175, 200, 225, 250, 275, 300, 325, 350, 375, 400, 425, 450 or 475 μm), although smaller (e.g., less than 90 μm) and larger (e.g., greater than 500 μm) beads may be used. As used herein, the term "container" refers to any structure that can hold or transfer cells (e.g., an eppendorf tube or other type of tube, a flask, a cylinder, a well, tubing, or other type of material used to hold or transfer cells). Surfaces modified according to the invention include silica materials as well as non-silicon materials such as zirconium and yttrium.

The invention provides a variety of compositions comprising modified surfaces. In some embodiments, the invention provides modification of the surface of any component conventionally utilized in the process of cell disruption and/or lysis (e.g., carried out to recover and/or isolate nucleic acid from the cell), and compositions comprising the same. For example, containers, beads, pipette tips, and other materials utilized for cell disruption and/or lysis may be modified according to the invention. The invention is not limited by the type of modification made to a surface. In some embodiments, any modification (e.g., chemical modification) that reduces the affinity of nucleic acid (e.g., DNA or RNA) to attach to and/or become adsorbed onto a surface may be used. In a preferred embodiment, modification of a surface is carried out with an agent that replaces reactive —OH bonds on the surface of a substance used for cell disruption (e.g., beads or container surface) with a fluorinated organic molecule (e.g., that is not reactive with nucleic acid (e.g., that does not adsorb nucleic acid upon its surface)). Although an understating of a mechanism of action is not needed to practice the invention, and while the invention is not limited to any particular mechanism of action, in some embodiments, replacing OH— bonds on a surface (e.g., Si—OH, or Si—O— bonds (e.g., that come into contact with nucleic acid released from a cell)) with a fluorinated organic molecule reduces or eliminates the amount of nucleic acid that interacts with (e.g., that attaches to or otherwise becomes absorbed and/or adsorbed to) the surface. Thus, the invention reduces the presence and/or number of surface —OH moieties on unmodified surfaces (e.g., bead or container surface) that are involved in nucleic acid binding (e.g., DNA binding through intermediate salt bridges) thereby increasing the overall recovery of nucleic acid from a sample.

Accordingly, in some embodiments, materials containing a fluorinated surface of the invention find particular use in cell lysis and/or cell disruption procedures (e.g., mechanical stressing of cells). Compositions comprising a fluorinated surface of the invention also find use with other methods used to disrupt and/or lyse cells including, but not limited to, freeze-thaw cycling, sonication, chemical treatment, heating, and other methods known in the art. In some embodiments, use of one or more compositions comprising a fluorinated surface (e.g., beads and/or container surfaces) of the invention enhance the amount of nucleic acid recovery post cell disruption and/or lysis (e.g., via reducing undesired DNA/RNA adsorption on a bead and/or container surface).

Thus, the invention provides the ability to detect nucleic acid samples (e.g., DNA and/or RNA (e.g., from a microbe) not previously detectable in a sample (e.g., whole blood, sputum, bronchoalveolar lavage, sterile fluids, and environmental samples (e.g., non biological fluids such as buffers or water samples (e.g. seawater, wastewater, drinking water))). Compositions and methods of the invention are useful for recovery of nucleic acid from bacterial, fungal, plant, and animal cells, as well as from viral particles and bacterial spores. In some embodiments, use of compositions and methods of the invention increase the amount of nucleic acid recoverable from a sample (e.g., whole blood, sputum, bronchoalveolar lavage, sterile fluids, environmental samples such as buffers or water samples, bacterial, fungal, plant, and animal cells, viral particles and bacterial spores), by about 10%, 25%, 30%, 40%, 50%, 60%, 70%, 80%, 90%, 100%, 110%, 120%, 130%, 150%, 170%, 200%, 220%, 240%, 260%, 280%, 300%, 325%, 350%, 375%, 400%, 450%, 500%, 550%, 600% or more. Data generated during development of embodiments of the invention have shown enhanced recovery of nucleic acid ranging from 125% to 334% DNA recovery compared to the same procedure using unmodified surfaces (e.g., bead surfaces). For example, experiments were conducted during development of embodiments of the invention wherein conventional lysis technology using non-modified glass beads were used for mechanical lysis by mechanical disruption with nucleic acid harvested and compared to lysis using zirconium or zirconium yttrium beads (ZY beads) as well as perfluorooctyltriethoxysilane treated ZY beads. ZY beads have improved surface chemistry (e.g., fewer —OH reactive groups) compared to standard glass silica beads but still have significant amounts of DNA adsorption due in part to the remaining substrate-OH moieties. Results demonstrated that a greater amount of DNA was recovered using ZY beads compared to standard glass silica beads, but that the best recover was observed using perfluorooctyltriethoxysilane treated beads.

Thus, the invention provides compositions and methods that reduce/remove moieties that react with DNA/RNA (e.g., —OH moieties) by chemical modification thereby decreasing the surface energy of the beads (e.g., by adding fluorinated organo-silane compounds to the surface). An exemplary flow chart is provided in FIG. 1 that describes a generalized sample work flow in the analysis of samples for DNA/RNA molecules. The boxes highlight that cell lysis is the first step in sample preparation and an improvement at this stage leads to an exponential increase in signal post-PCR. Thus, the invention provides that for samples that have low concentrations (e.g., those observed in blood stream infections), compositions and methods of the invention provide that ability to detect and characterize samples previously below limits of detection (e.g., thereby increasing the ability to diagnose and/or characterize patients).

Compositions and methods of the invention are useful with any type of bead beating technology used to lyse cells (e.g., bacterial cells) across all areas of research and diagnostics (e.g. sepsis, food borne pathogens, biodefense, forensics, etc.). Moreover, compositions and methods of the invention are useful for preparation of all samples that are currently processed in art recognized normal concentration ranges; however, in a preferred embodiment, compositions and methods of the invention find particular utility for sample preparation (e.g., extraction and/or isolation of nucleic acid) with low quantity and/or quality samples approaching stochastic sampling limits).

Thus, the compositions and methods described herein can be used in any process that uses mechanical agitation (e.g., bead beating or facsimiles thereof) to lyse cells (e.g., for use in molecular diagnostics, forensics, tumor cell analysis, food borne pathogens, and biowarfare detection). The invention provides improvement to DNA recovery from a cell or cells of interest (e.g., human/bacterial/fungal) from all fluid types that can be sampled/tested (e.g., whole blood or serum for sepsis and blood stream infections, sputum, cerebral spinal fluid, etc.). All protocols/assays that use cell lysis as a sample preparation technique benefit from the compositions and methods disclosed herein. This invention can be applied to a bulk amount of beads or can be applied to individual prepackaged tubes. A bulk preparation of grams to several kilograms of beads can be accomplished with benchtop sized glassware, a stirbar, and reagents. Large scale manufacturing is accomplished with moderately sized reactors. The additional manufacturing costs associated with applying the invention to creating consumable units (about 500 mg to 10 grams of beads) are minimal (outside of reagent cost/overhead/labor). Modified beads can be added to any tube at the same mass as a user would currently use with unmodified beads. Prepackaged tubes can contain the same amount of beads but with improved performance compared to non-modified beads. Modified beads of the invention can also be packaged into other mechanical lysis technologies that use beads (e.g., the Claremonet Biosolutions Omnilyser).

In some embodiments, a modifying reagent of the invention (e.g., (1H,1H,2H,2H)Perfluorooctyltriethoxysilane) is added directly to a component used for cell disruption and/or lysis (e.g., to a container (e.g., an eppendorf tube or other type of tube, a well, tubing, or other type of material used to hold or transfer cells) or beads (e.g., beads used for mechanical beating or stressing of cells) and allowed to react (e.g., in order to modify the surface of the container and/or beads). In some embodiments, a modifying reagent of the invention is added to or combined with a dispersing reagent (e.g., a solvent (e.g., toluene)) and then added to a component used for cell disruption and/or lysis (e.g., in order to improve surface coverage and/or reaction efficiency).

The invention is not limited by the type of material (e.g., bead or container surface) modified (e.g., using compositions and/or methods of the invention (e.g., in order to generate compositions comprising modified surfaces of the invention)). For example, modification of bead surfaces may be made to a variety of bead types including, but not limited to, beads made with silica (e.g., manufactured as fused quartz, crystal, fumed silica or pyrogenic silica, colloidal silica, silica gel, aerogel, glass, fiber (e.g., optical fiber), cement and ceramics (e.g., earthenware, stoneware, and porcelain), zirconium, zirconium silica, zirconium yttrium, and all other related glass oxide and mixtures of glasses and oxides.

In some embodiments, a modifying reagent comprises reactive groups (e.g., triethoxy groups) that react with surface —OH groups (e.g., on a bead surface or container surface) creating a covalent bond that releases one ethanol group per surface site (e.g., —OH group) reacted. In one embodiment, triethoxy groups of perfluorooctyltriethoxysilane react (e.g., via standard silane reaction) with substrate-OH groups on a surface (e.g., substrate surface (e.g., bead or container surface)) creating a covalent bond and releasing one ethanol group per surface site reacted as depicted in the following chemical reaction:

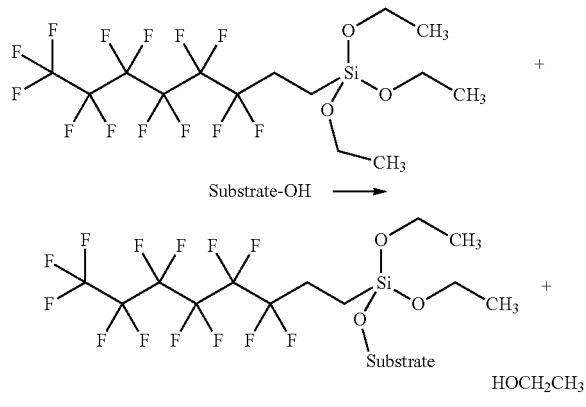

Compositions comprising modified surfaces of the invention find use in a method for lysing prokaryotic or eukaryotic cells, or for the simultaneous lysis of both prokaryotic and eukaryotic cells. Compositions comprising modified surfaces of the invention find use in multiple lysing techniques including, but not limited to, sonication, mechanical vortex centrifugation, or magnetic vortex centrifugation.

Modified surfaces of the invention may be of any suitable composition or material, for example plastic materials. Suitable plastics may be porous or non-porous depending upon the degree of cross-linking in the polymer and include polystyrene, styrene acrylate co-polymer, polystyrene cross-linked with divinylbenzene, polyvinyltoluene, polymethacrylate and polycarbonate. Alternative materials include polysaccharides (such as dextran), metal oxides (such as aluminium oxide), silica and carbon Any type of cell may be used with the compositions and methods of the invention. The nature and source of the cells is not critical to the invention. That is, cells from any source may be used, including plant cells, animal cells and microbial (e.g., bacterial, fungal, viral and yeast) cells. For example, samples from which nucleic acid is harvested/isolated using the compositions and methods of the invention may be any material containing nucleic acid, including for example foods and allied products, clinical and environmental samples. However, the sample will generally be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, urine, faeces, cerebrospinal fluid or any other body fluids, tissues, cell cultures, cell suspensions etc.

Harvesting/isolating DNA from cells lysed using the compositions and methods of the invention may be performed using any of the many known methods in the art (e.g., affinity purification, magnetic separation, organic extraction, filtering, etc.). The nucleic acid may be DNA, RNA or any naturally occurring or synthetic modification thereof, and combinations thereof. Preferably however the nucleic acid will be DNA, which may be genomic, or, cDNA, and single or double stranded or in any other form. Where the method of the invention is used to isolate DNA, it may be coupled with a further step to isolate RNA from the same sample.

EXPERIMENTAL

The following examples are provided in order to demonstrate and further illustrate certain preferred embodiments and aspects of the present invention and are not to be construed as limiting the scope thereof.

Example 1

Basic Reaction

To an existing tube of beads used for cell lysis (e.g. a tube containing ZY beads) add perfluorooctyltriethoxysilane. In one embodiment, to 900 mg of beads, 100 microliters of perfluorooctyltriethoxysilane is added. Agitate components. Allow reaction to proceed for 30 minutes to 1 hour at room temperature. Use beads without further purification.

Example 2

Purification

To an existing tube of beads used for cell lysis (e.g. a tube containing ZY beads) add perfluorooctyltriethoxysilane. In one embodiment, to 900 mg of beads, 100 microliters of perfluorooctyltriethoxysilane is added. Allow the reaction to proceed for 30 minutes to 1 hour at room temperature. Agitate components. Remove excess reagent and byproducts through heating with reduced pressure or lyophilization.

Example 3

Increased Reaction Time

To an existing tube of beads used for cell lysis (e.g. a tube containing ZY beads) add perfluorooctyltriethoxysilane. In one embodiment, to 900 mg of beads, 100 microliters of perfluorooctyltriethoxysilane is added. Allow the reaction to proceed overnight at room temperature. Agitate components. Remove excess reagent and byproducts through heating with reduced pressure or lyophilization.

Example 4

Use of Higher Temperature to Increase Extent of Reaction

To an existing tube of beads used for cell lysis (e.g. a tube containing ZY beads) add perfluorooctyltriethoxysilane. In one embodiment, to 900 mg of beads, 100 microliters of perfluorooctyltriethoxysilane is added. Allow the reaction to proceed 30 minutes to overnight at an elevated temperature (e.g., 50° C. or 70° C.). Agitate components. Remove excess reagent and byproducts through heating with reduced pressure or lyophilization.

Example 5

Use of a Dispersing Agent to Uniformly React with Surfaces

Create a stock solution of perfluorooctyltriethoxysilane dissolved in a dispersing reagent (e.g. toluene) at a prescribed concentration (e.g., 100 microMolar to greater than or equal to 1 Molar). To an existing tube of beads used for cell lysis (e.g. a tube containing ZY beads) add perfluorooctyltriethoxysilane stock solution. In one embodiment, to 900 mg of beads, 100 microliters of perfluorooctyltriethoxysilane stock solution is added. Allow the reaction to proceed 30 minutes to overnight at an elevated temperature (e.g. 50° C. or 70° C.). Agitate components. Remove excess reagent and byproducts through heating with reduced pressure or lyophilization.

Example 6

Use of a Catalyst or Reaction Promoter

Create a stock solution of perfluorooctyltriethoxysilane dissolved in a dispersing reagent (e.g. toluene) at a prescribed concentration (e.g. 100 microMolar to greater than or equal to 1 Molar). To an existing tube of beads used for cell lysis (e.g. a tube containing ZY beads) add perfluorooctyltriethoxysilane stock solution. In one embodiment, to 900 mg of beads, 100 microliters of perfluorooctyltriethoxysilane stock solution is added. To the same tube add either a catalyst or another chemical reagent to remove the secondary reaction product. (e.g., if the reagent is a trichlorofluorinated silane, a base is utilized to neutralize the HCl byproduct from the reaction and improve yield by LeChatellier's principle). Alcohols (from a triethoxy fluorinated silane) are removed by similar principles. Allow the reaction to proceed 30 minutes to overnight at an elevated temperature (e.g., 50° C. or 70° C.). Agitate components. Remove excess reagent and byproducts through heating with reduced pressure or lyophilization.

Example 7

Vapor Phase Reaction

The reagent may or may not be added to a dispersing reagent and then allowed to react with beads in the vapor phase. The reagent may or may not be heated and reduced or elevated pressures may be used in the atmosphere. A drying agent may be used to treat the air. Purification can be done in similar manners as the liquid phase methods described above. Larger scale reactions are created by the same examples listed above with the replacement of a tube of beads with another container filled with a larger scale amount of beads. For example, a 1 liter round bottom flask is utilized to prepare 1000 fold the amount of beads compared to the same tube discussed above. Larger scale manufacturing can be accomplished by similar reactor sizes/volumes as other commercial chemical productions.

While there described herein certain specific embodiments of the invention, it will be manifest to those skilled in the art that various modifications and rearrangements of the parts may be made without departing from the spirit and scope of the underlying inventive concept and that the same is not limited to the particular forms herein described.

What is claimed is:

1. A method of isolating a nucleic acid from a sample comprising: a) contacting the sample with a composition comprising a fluorinated organic group modified surface wherein said composition comprising said fluorinated organic group modified surface has less affinity for said nucleic acid than an identical composition without said fluorinated organic group modified surface; b) mechanically disrupting the sample; and c) isolating the nucleic acid from the disrupted sample.

2. The method of claim 1, wherein the composition comprising the modified surface is a silica bead.

3. The method of claim 2, wherein the bead is between 90 µm and 500 µm in size.

4. The method of claim 1, wherein the fluorinated organic group is a fluorinated silane.

5. The method of claim 4, wherein the fluorinated silane is a perfluorooctyltriethoxysilane.

6. The method of claim 1, wherein the nucleic acid is a DNA.

7. The method of claim 1, wherein the sample is a mammalian or a microbial cell.

8. The method of claim 1, wherein said composition comprising a fluorinated organic group modified surface is a bead surface.

9. The method of claim 8, wherein said mechanically disrupting the sample is bead beating.

10. The method of claim 9, wherein said composition comprises a dispersing agent.

11. The method of claim 10, wherein said dispersing agent is toluene.

12. The method of claim 9, wherein said composition comprises a catalyst or reaction promoter.

13. The method of claim 12, wherein said reaction promoter is a base.

* * * * *